(12) United States Patent
Schaffran et al.

(10) Patent No.: US 8,460,306 B2
(45) Date of Patent: Jun. 11, 2013

(54) SURGICAL SCREW RETENTION CLIP AND METHOD OF USING THE SAME

(75) Inventors: Allan Schaffran, Toronto (CA); Andy Doug-Lun Wong, Toronto (CA); Robert G. Dickie, King City (CN)

(73) Assignee: Pure Dental Logic Inc., Toronto, Ontario (CA)

( * ) Notice: Subject to any disclaimer, the term of this patent is extended or adjusted under 35 U.S.C. 154(b) by 1619 days.

(21) Appl. No.: 11/703,968

(22) Filed: Feb. 8, 2007

(65) Prior Publication Data

US 2008/0154281 A1 Jun. 26, 2008

Related U.S. Application Data

(63) Continuation-in-part of application No. 11/644,719, filed on Dec. 22, 2006, now Pat. No. 7,806,692, and a continuation-in-part of application No. 11/446,700, filed on Jun. 5, 2006.

(51) Int. Cl.
*A61B 17/88* (2006.01)
*B25B 23/10* (2006.01)

(52) U.S. Cl.
USPC ........... 606/104; 606/302; 606/306; 606/916; 81/452

(58) Field of Classification Search
USPC ............... 606/104, 916, 86 B, 302, 303, 306, 606/308, 322, 328; 433/153, 155; 81/451–458, 81/461, 180.1; 411/407, 999
See application file for complete search history.

(56) References Cited

U.S. PATENT DOCUMENTS

| | | | |
|---|---|---|---|
| 302,067 A * | 7/1884 | Wallen | 81/454 |
| 538,508 A * | 4/1895 | Eberhart | 227/149 |
| 1,127,236 A | 2/1915 | Harbridge | |
| 1,712,196 A | 5/1929 | Burger et al. | |
| 2,444,287 A * | 6/1948 | Ettinger | 81/455 |
| 3,604,488 A | 9/1971 | Wishart et al. | |
| 4,704,929 A | 11/1987 | Osada | |

(Continued)

FOREIGN PATENT DOCUMENTS

| | | |
|---|---|---|
| WO | WO 97/06930 | 2/1997 |
| WO | WO 97/24996 | 7/1997 |

(Continued)

*Primary Examiner* — Michael T Schaper
(74) *Attorney, Agent, or Firm* — Sand & Sebolt

(57) ABSTRACT

A clip for retaining a screw on a tip of a screwdriver shaft. The clip comprises a housing that has a first end and a second end and a longitudinal axis extending therebetween. The housing includes a longitudinal bore that is accessible from both the first and second ends of the housing. A pair of jaw members is provided on the housing proximate the first end thereof. The jaw members surround a first portion of the bore and are configured to capture and retain a length of the screwdriver shaft therebetween. A pair of clamping members is formed on the housing proximate the second end thereof. The clamping members surround a second portion of the bore and are configured to capture a head of the surgical screw therebetween. During use, the screwdriver shaft is pushed downwardly and twisted slightly within the bore to engage the head of the screw. The screw is threadably engaged in a pre-drilled hole in the patient's bone. When the screw is sufficiently engaged to prevent it from accidently being dislodged, the clip is disengaged from the screw. The retaining clip prevents the screw from accidentally dropping off the screwdriver and allows the surgeon to use a single hand to install the screw.

17 Claims, 10 Drawing Sheets

U.S. PATENT DOCUMENTS

| | | | |
|---|---|---|---|
| 4,744,273 | A | 5/1988 | Bartok, Jr. |
| 5,158,458 | A | 10/1992 | Perry |
| 5,423,860 | A | 6/1995 | Lizardi et al. |
| 5,462,436 | A * | 10/1995 | Beaty .................... 433/141 |
| 5,515,755 | A * | 5/1996 | Kung ..................... 81/452 |
| 5,692,904 | A | 12/1997 | Beaty et al. |
| 5,927,979 | A | 7/1999 | Misch et al. |
| 6,116,125 | A | 9/2000 | McLeod |
| 6,244,141 | B1 | 6/2001 | Han |
| 6,280,192 | B1 | 8/2001 | Groll et al. |
| 6,328,746 | B1 * | 12/2001 | Gambale ................ 606/104 |
| 6,701,812 | B1 * | 3/2004 | Sawamura ............. 81/453 |
| 6,854,972 | B1 | 2/2005 | Elian |
| 6,997,086 | B1 | 2/2006 | Graham |
| 7,100,476 | B1 | 9/2006 | Feit |
| 7,661,957 | B2 * | 2/2010 | Tanimura ............... 433/173 |
| 2005/0149053 | A1 * | 7/2005 | Varieur et al. ......... 606/104 |
| 2005/0266379 | A1 | 12/2005 | Kumar et al. |
| 2006/0075856 | A1 | 4/2006 | Tilton |
| 2006/0217738 | A1 * | 9/2006 | Tanimura ............... 606/104 |
| 2006/0278050 | A1 | 12/2006 | Hsiao |
| 2007/0295173 | A1 | 12/2007 | Swartz |

FOREIGN PATENT DOCUMENTS

| | | |
|---|---|---|
| WO | WO 00/28914 | 5/2000 |
| WO | WO 03/037207 | 5/2003 |
| WO | WO 03/101332 | 12/2003 |
| WO | WO 2004/093714 | * 11/2004 |

* cited by examiner

SURGICAL SCREW RETENTION CLIP AND METHOD OF USING THE SAME

CROSS-REFERENCE TO RELATED APPLICATIONS

This is a Continuation-in-Part of U.S. patent application Ser. No. 11/446,700 filed Jun. 5, 2006, and a Continuation-in-Part of U.S. patent application Ser. No. 11/644,719, filed Dec. 22, 2006, the entire specifications of which are incorporated herein by reference.

BACKGROUND OF THE INVENTION

1. Technical Field

This invention generally relates to surgical implements and procedures. More particularly, the invention relates to a device for installing surgical screws and a method of using the same. Specifically, the invention relates to a clip for retaining a surgical screw on the tip of a screwdriver shaft.

2. Background Information

Very small screws are frequently used in surgical procedures to secure components together. These procedures include dental reconstruction of the mandible or surgery on hands or other small bone body regions. In mandible surgeries, for example, where the jawbone is damaged and the surgeon must reinforce and stabilize the bone with special multi-holed titanium plates, tiny titanium screws are used to secure the plates to the jawbone. Surgeries of this type typically are conducted using a special tool kit that is delivered to the operating room in a sterile condition. The tool kit will include an assortment of plates, plate benders, cutters, screwdrivers and a full assortment of screws. The kit may include drawers that store all of these components. A mandible kit, for example, would include a screw caddy or insert tray that typically will have storage for thirty-six 2.0 mm screws of various lengths and thirty-six 2.4 mm screws of various lengths. The screws are all retained tip down in the holes in the plastic tray and each hole has a sequential number for each screw diameter. Just the head of the screw sticks up about around ⅛" or 3 mm above the numbered surface of the tray. Furthermore, the groups of each screw length are slightly separated from the others to aid selection of the length as the rest of the screw is not visible to the surgical staff. The sequential numbering is important as the surgical team conducts a count of the screws missing from the tray verses how many screws are visible in the patient prior to closing up the patient's tissue and skin.

During surgery, the surgeon first bends and adjusts a titanium plate to the bone's anatomical surface and then, holding the fitted plate in place, drills a small hole in the bone through one of the holes in the plate. The surgical staff person who is assisting the surgeon takes a tiny titanium screw from the caddy. The screw may be as small as 2.0 mm in diameter and between 4.0 mm and 18.0 mm in length. The screw is positioned and balanced on the tip of a dental screwdriver and then the driver is passed to the surgeon. The surgeon must then hold the plate in place and try to engage the screw in the bone.

The surgical screws used in these procedures tend to have very shallow heads so as not to create bumps in the skin. Furthermore, most of the screws do not have socket type drives but, instead, have a very shallow X-shaped groove that tends to cause axial misalignment of the screw to the driver. Consequently, there is not much interlocking engagement between the screw and driver to aid in holding the screw on the tip thereof. Furthermore, surgical screws are not self-tapping as the tip may need to protrude through to the opposite side of the patient's bone. The lack of a pointed tip on the screws also adds to the surgeon's challenges in lining the screw up with the hole in the bone and in beginning to engage the screw threads in the bone. Surgeons complain of the enormous quantity of time wasted due to the operating room staff dropping screws as they pass the driver to the surgeon. They also complain of their need to use only one hand to operate the driver and start the screw in the drilled hole as their other hand is occupied in stabilizing the plate on the bone. The need to keep the screw on the tip of the driver while at the same time angling the driver to insert the screw tip into the drilled hole, also frequently results in the surgeon themselves dropping the screws into the patient's body. Any dropped or lost screws in the body cavity will absolutely cause infection and complications and potential liability issues and these screws have to be located and removed. The surgeon must then pass the driver back to the surgical staff and wait for them to load a new screw onto the driver so that they can attempt the procedure yet again. Aids like wax are often used in an attempt to retain the screws on the driver tips. Apart from being a questionable practice from a sterility aspect, the wax tends to also cause the driver to slide and slip on the screw head when the screw is being tightened, making installation more difficult. Rarely does a complex surgical procedure go by without at least one screw being dropped. The dropped screws cannot be used as they are no longer sterile and must be put aside and retained for the final screw count. Considering that these titanium screws each cost around $50 or more and that a typical mandible surgery, for example, can require ten to sixteen screws, the financial cost of the dropped screws, together with the cost in time lost in dropping and engaging new screws, tends to add substantially to the spiraling costs of healthcare.

There is therefore a need in the art for an improved system for engaging surgical screws with screwdrivers and for retaining the same in place until the tips of the screws are captured in the bone.

SUMMARY OF THE INVENTION

The device of the present invention is clip for retaining a screw on a tip of a screwdriver shaft. The clip comprises a housing that has a first end and a second end and a longitudinal axis extending therebetween. The housing includes a longitudinal bore that is accessible from both the first and second ends of the housing. A pair of jaw members is provided on the housing proximate the first end thereof. The jaw members surround a first portion of the bore and are configured to capture and retain a length of the screwdriver shaft therebetween. A pair of clamping members is formed on the housing proximate the second end thereof. The clamping members surround a second portion of the bore and are configured to capture a head of the surgical screw therebetween. During use, the screwdriver shaft is pushed downwardly and twisted slightly within the bore to engage the head of the screw. The screw is threadably engaged in a pre-drilled hole in the patient's bone. When the screw is sufficiently engaged to prevent it from accidently being dislodged, the clip is disengaged from the screw. The retaining clip prevents the screw from accidentally dropping off the screwdriver and allows the surgeon to use a single hand to install the screw.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims. Throughout the drawings, like numerals refer to similar components.

DETAILED DESCRIPTION OF THE INVENTION

Figure 1:
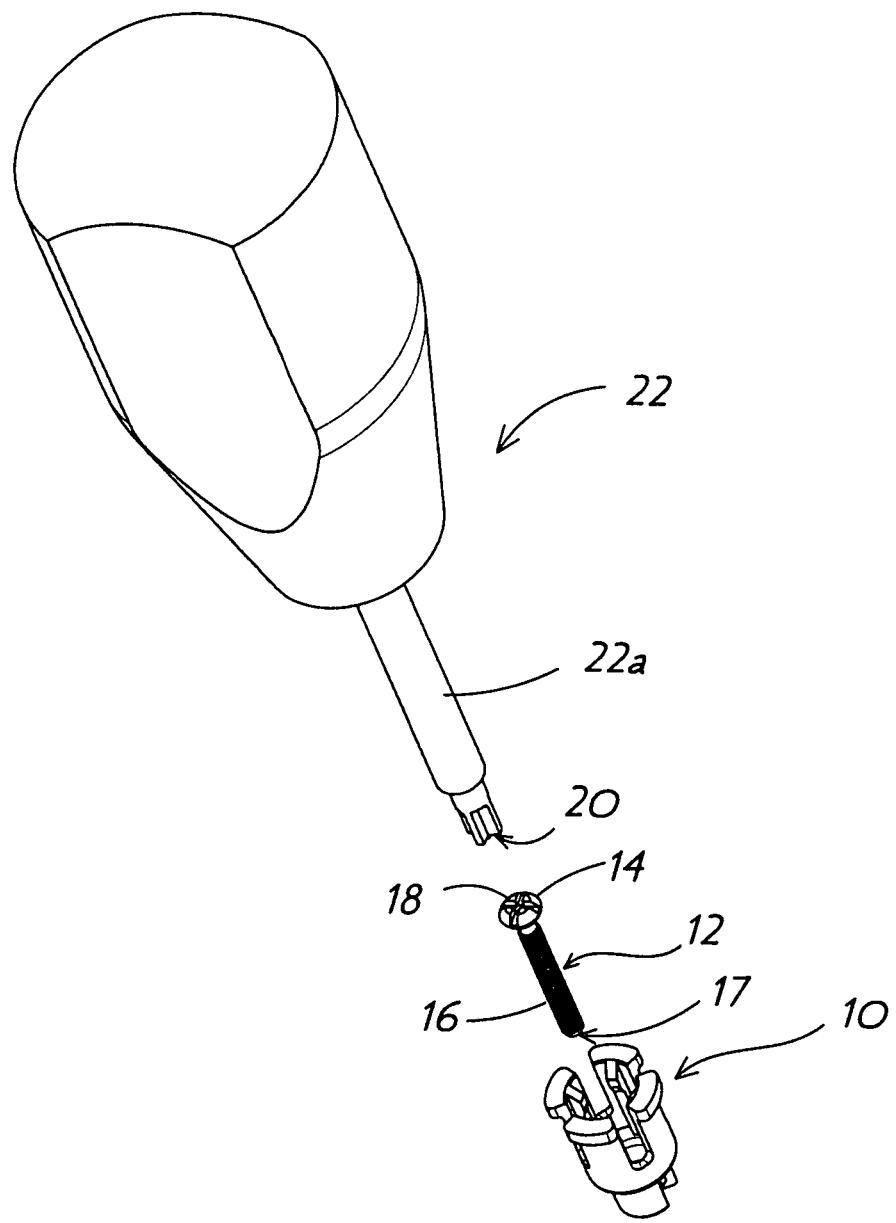
FIG. 1 is an exploded perspective view of a screwdriver, surgical screw and retention clip in accordance with the present invention.
Figure 2:
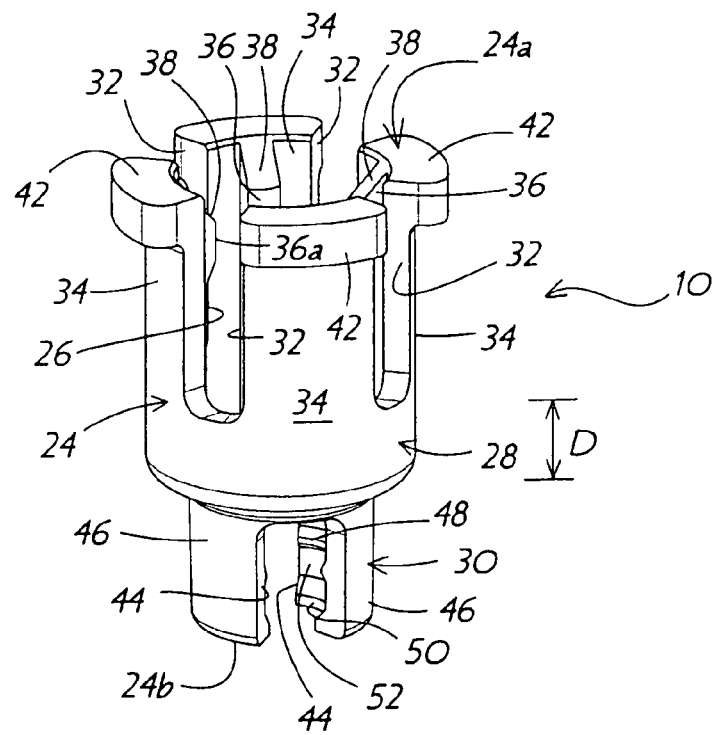
FIG. 2 is a perspective view of the retention clip in accordance with the present invention.

Referring to FIGS. 1-4, there is shown a retention clip in accordance with the present invention and generally indicated at 10. Clip 10 is contemplated for use in any general surgeries, such as surgeries on the lower jaw, hands or small bones of a patient's body. Clip 10 is configured to receive a surgical screw 12 therein and to retain the same on a tip 20 of a screwdriver 22. As shown in FIG. 1, screw 12 has a head 14 and shaft 16, with head 14 including the typical X-shaped grooves 18 therein for engagement by tip 20. Clip 10 substantially prevents screw 12 from accidentally disengaging from tip 20 of screwdriver 22.

In accordance with a specific feature of the present invention, retention clip 10 is injection molded from a suitable material such as acrylonitrile butadiene styrene (ABS) plastic. Clip 10 may be manufactured in any one of a range of colors, with the colors being selected to indicate that the clip is holding a screw of a particular size.

Clip 10 comprises a generally tubular member having an exterior wall 24 that surrounds and defines an interior bore 26. Wall 24 has a first end 24a (FIG. 3) and a second end 24b and has a longitudinal axis "Y" extending between first and second ends 24a, 24b. Wall 24 is shaped to form a first section 28 and a second section 30. Wall 24 comprises a first section 28 having first exterior diameter "W1" (FIG. 3) and second section 30 having a second exterior diameter "W2", with "W2" being smaller than "W1". Furthermore, the diameter of bore 26 is greater in first section 28 than the diameter of bore 26 in second section 30. Bore 26 may be accessed through openings in both first end 24a and second end 24b, but the opening at second end 24b is substantially smaller than that at first end 24a, being sized only to permit the shaft 16 of screw 12 therethrough.

Wall 24 defines a plurality of longitudinal U-shaped slots 32 in first section 28. Slots 32 extend from first end 24a downwardly toward second end, terminating a distance "D" (FIG. 3) inwardly from second section 30. In the preferred embodiment, there are four such slots 32 and, consequently, first section 28 is divided into four jaw members 34 that circumscribe bore 26. Because clip 10 is manufactured from a flexible material, jaw members 34 are able to flex slightly outwardly away from the center "C" (FIG. 4) of clip 10 when the shaft 22a and tip 20 of screwdriver 22 are inserted therein as will be hereinafter described. The interior surface of wall 24 in first section 28 is also provided with a plurality of ribs 36, each rib 36 being centrally formed on one of the jaw members 34. A top end 38 of each rib 36 is angled downwardly and inwardly into bore 26. The ribs 36 therefore act as a guide for tip 20 of screwdriver 22 when it is inserted into bore 26. Ribs 36 extend from proximate top end 24a of first section 28 to a shoulder 40 intermediate first and second sections 28, 30. Each rib 36 is provided with an outwardly extending protrusion 36a that effectively narrows bore 26 in the vicinity of protrusions 36a. Alternatively, an O-ring (not shown) may be inserted proximate first end 24a of clip 10 to narrow bore 26 and provide a frictional engagement between shaft 22a and clip 10. Finally, an outwardly extending flange 42 is provided on each jaw member 34 proximate top end 24a. Flanges 42 provide a gripping surface by which clip 10 may be more easily held by the surgeon.

Figure 3:
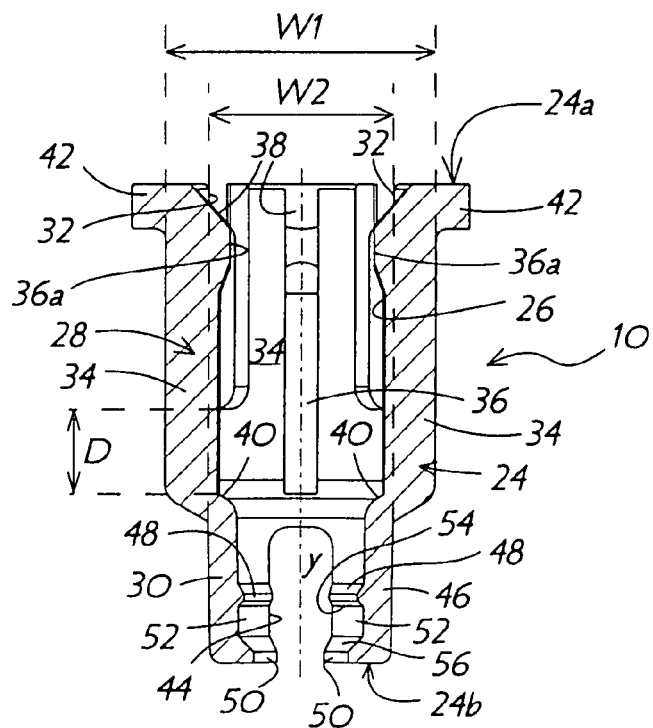
FIG. 3 is a cross-section of the retention clip of FIG. 2.
Figure 4:
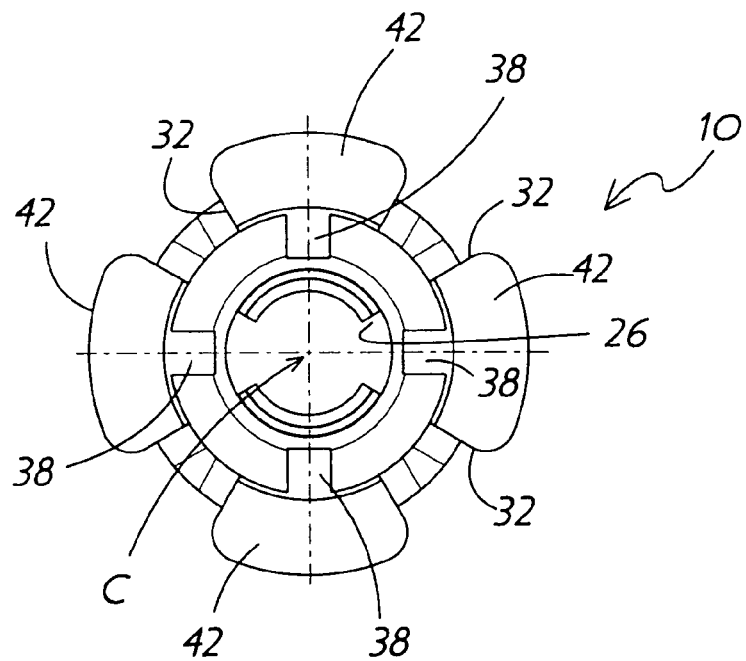
FIG. 4 is a top end view of the clip of FIG. 2.
Figure 5:
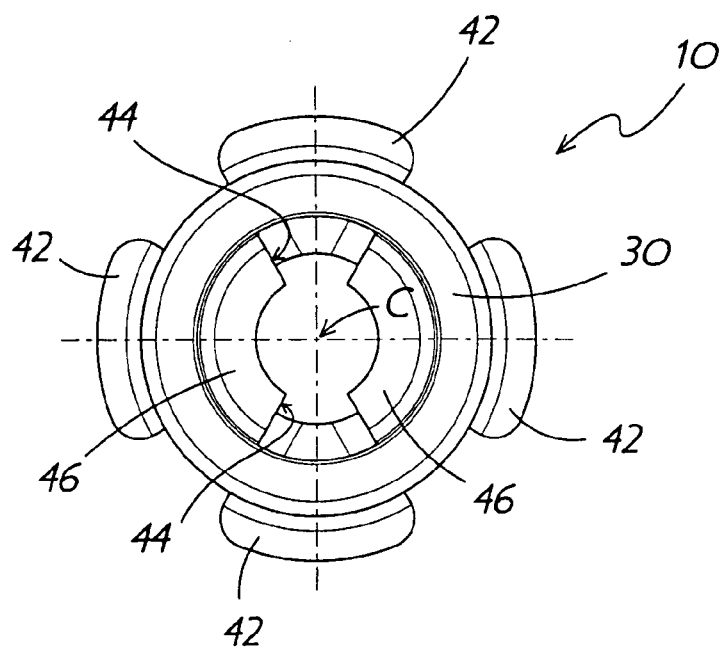
FIG. 5 is a bottom end view of the clip of FIG. 2.

Second section 30 defines at least two substantially U-shaped slots 44 therein that are positioned in opposition to each other as shown in FIG. 5 and that are longitudinally aligned with the longitudinal axis of housing 24. Second section 30 is thereby formed into two clamping members 46 that circumscribe bore 26. Clamping members 46 flex outwardly away from each other when screw head 14 is removed therefrom. The flexing movement of clamping members 46 is considerably smaller than the movements that jaw members 34 may undergo. The interior surface of each clamping member is provided with two spaced apart rings or flanges 48, 50 that are separated from each other by a channel 52. Channel 52 is sized to receive head 14 of screw 12 therein. Flanges 48, 50 are disposed substantially at right angles to the longitudinal axis "Y" of clip 10 and both flanges 48 and 50 cause bore 26 to be narrowed as shown in FIG. 3. Flanges 50 project further inwardly into bore 26 than flanges 48, thereby causing bore 26 to be narrowed to the greatest degree proximate thereto. Flanges 48 are each provided with a shoulder 54 and flanges 50 are each provided with a shoulder 56. Shoulders 54, 56 are angled to abut the upper and lower surfaces of head 14 of screw 12 when head 14 is received in channel 52. The angles of shoulders 54, 56 are such that head 14 becomes locked into channel 52 as will be hereinafter described.

Figure 6:
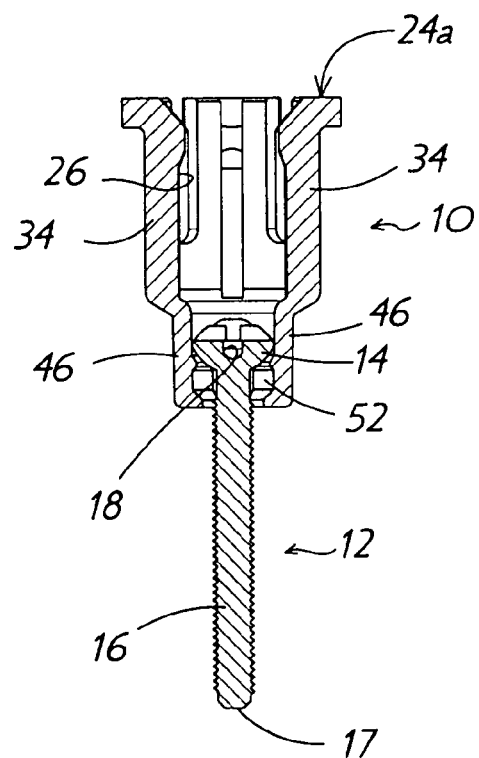
FIG. 6 is a cross-sectional front view of the retention clip of the present invention initially engaged with a surgical screw and showing the screw in an unlocked position within the clip.
Figure 7:
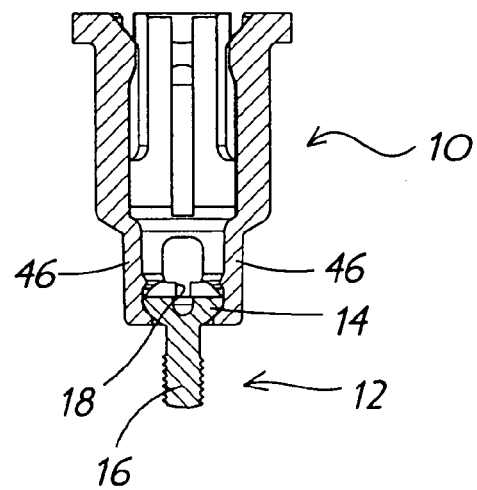
FIG. 7 is a cross-sectional front view of the retention clip with the screw locked into position within the clip.

FIGS. 6 and 7 illustrate how screw 12 is captured within clip 10. Tip 17 of screw 12 is inserted through the opening in the first end 24a of clip and into bore 26. Clip 10 is pushed downwardly around screw 12 until tip 17 of shaft 16 slides out of the opening in second end 24b of clip 10. This downward movement is continued until head 14 of screw 12 slides past rib 48 and into channel 52 between flanges 48 and 50. As head 14 slides past flanges 48, clamping members 46 flex slightly outwardly away from each other, allowing head 14 to move past the same. When head 14 slides into channel 52, clamping members snap back to their original position, thereby clamping head 14 therebetween. If a surgical staff member is engaging clip 10 with screw 12, they will know that screw 12 is in the locked position when they hear a snapping or clicking sound. Shoulder 56 on rib 50 prevents any further downward movement of clip 10. At this point, shown in FIG. 7, screw 12 is fully locked and retained within clip 12 and is ready for engagement by screwdriver 22. Screw 12 cannot fall out of either first or second end 24a, 24b of clip 10.

Figure 8:
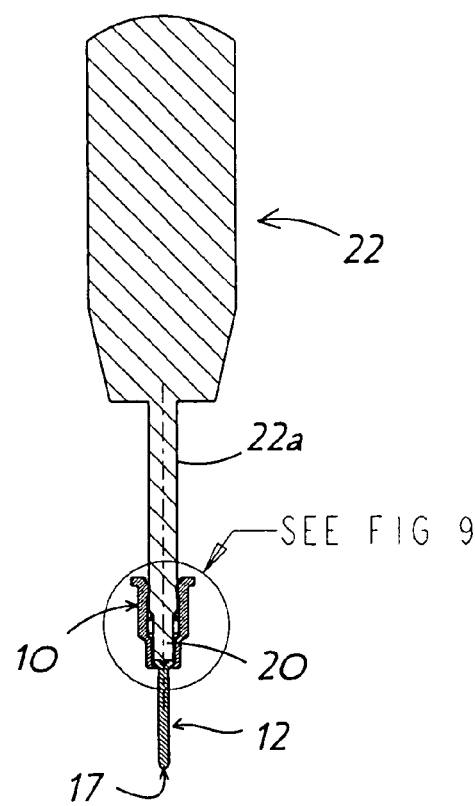
FIG. 8 is a cross-sectional front view of the screwdriver tip engaged with the screw via the retention clip.
Figure 9:
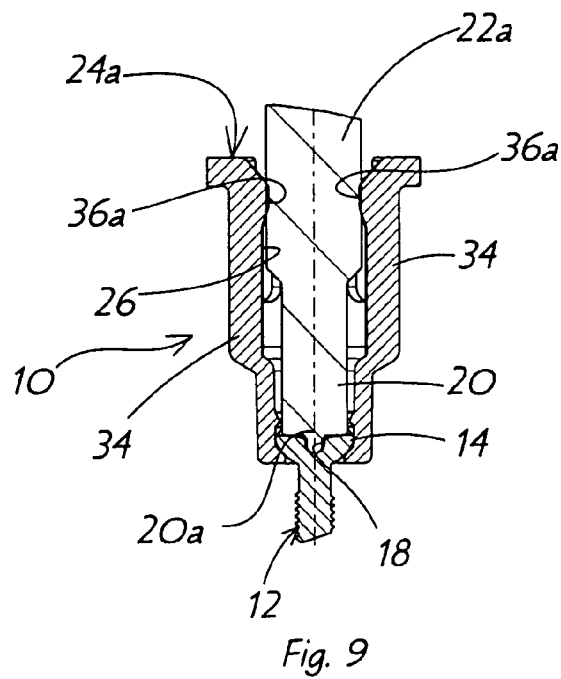
FIG. 9 is an enlarged cross-sectional front view of the highlighted region of FIG. 8.

FIGS. 8 and 9 illustrate how clip 10 and screw 12 are engaged by screwdriver 22. Tip 20 of shaft 22a of screwdriver 22 is inserted through the opening in first end 24a of clip 10. Tip 20 is small enough to pass through the gap between protrusions 36a on ribs 36. As shaft 22a engages protrusions 36a, jaw members 34 are pushed outwardly away from each other, thereby allowing tip 20 to continue to move downwardly to engage head 14 of screw 12. Jaw members 34 are flexed outwardly and therefore are biased into engagement with the outer surface of shaft 22a. Clip 10 thus frictionally engages shaft 22a. The complementary configured end 20a of tip 20 interlocks in the X-shaped grooves 18 in head 14. Thus, screw 12 is locked into clip 10 and clip 10 is frictionally engaged on shaft 22a of screwdriver 22. Clip 10 remains engaged on shaft 22a of screwdriver 22, no matter what orientation screwdriver 22 assumes.

Figure 10:
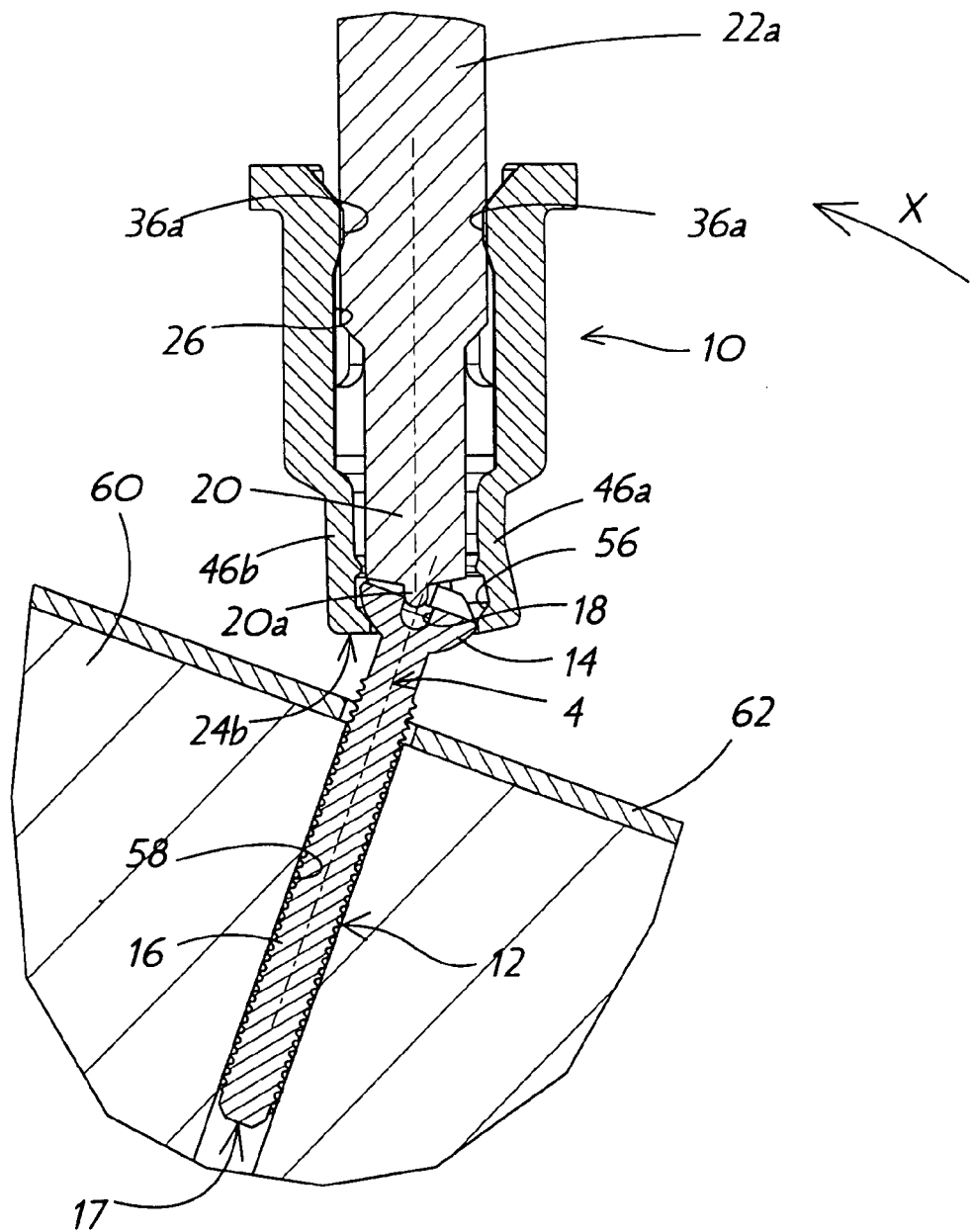
FIG. 10 is a cross-sectional front view of the tip of the screwdriver and retention clip being disconnected from the screw.
Figure 11:
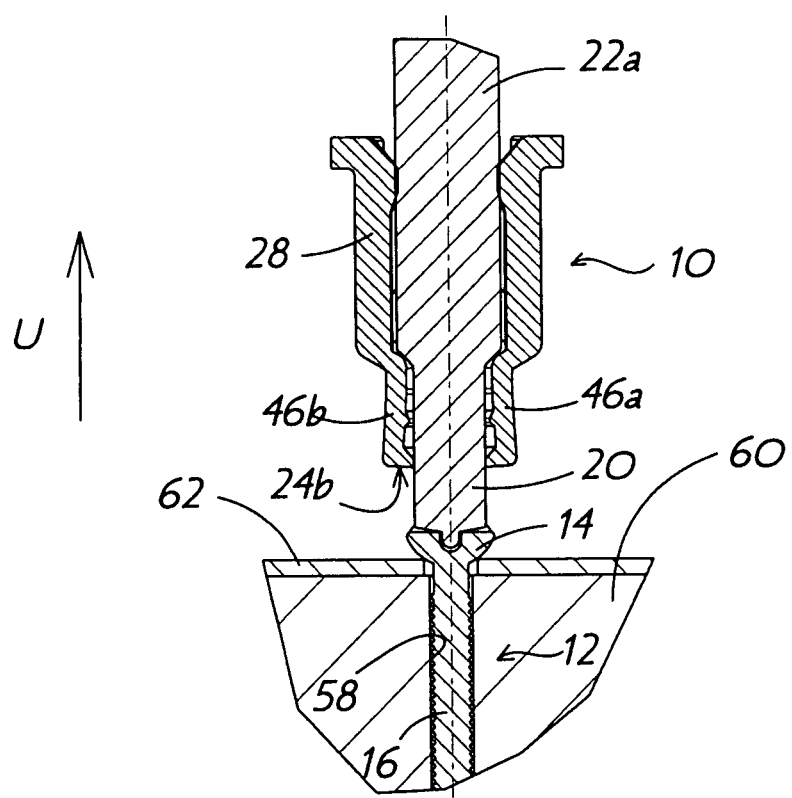
FIG. 11 is a cross-sectional front view of an alternative method for disconnecting the screwdriver and retention clip from the screw.

Screw 12 may now be used in the surgical procedure. It should be noted that screw 12 is not self-tapping as tip 17 of screw 12 may need to protrude through the opposite side of the patient's bone 60 (FIG. 11). Screw 12 therefore has to be installed into a pre-drilled hole 58 in bone 60. The lack of a pointed tip on screw 12 adds to the surgeon's challenges to line screw 12 upon with and centered in hole 58 and to maintain a reasonable axial alignment with the screw and hole, all while trying to start threading screw 12 therein. Once tip 17 is correctly positioned, screwdriver 22 is rotated about its longitudinal axis to drive screw 12 into bone 60. This motion is continued until screw 12 is sufficiently seated in bone 60 that it will not accidentally dislodge therefrom. Clip 10 may then be removed from engagement with screw 12. This may be done in one of two ways. The first way is illustrated in FIG. 10. This procedure enables a surgeon to use only one hand to both install screw 12 and to disconnect clip 10 therefrom once screw 12 has been sufficiently installed. In order to detach clip 10 from screw 12, the surgeon twists the handle of the screwdriver so that shaft 22a thereof moves out of alignment with the longitudinal axis "Y" of screw 12. This twisting motion is indicated by the arrow "X" in FIG. 10. The motion causes a portion of head 14 to ride along shoulder 56 of clip 10 and push the associated one of clamping members 46a away from the other of the clamping members 46b. The opening at second end 24b of clip is thereby expanded and head 14 of screw 12 slides out of the opening. At this point, the surgeon may completely remove clip 10 from screwdriver 22 by sliding clip 10 off the tip 20 thereof. Alternatively, the surgeon may simply grasp first section 28 of clip 10 and pull clip 10 up shaft 22a so that clip 10 is not in the way of the surrounding soft tissue and the surgeon has full visibility of the driver tip 20 to finish turning in screw 12. Once this has been completed, screwdriver 22 is passed back to the surgical staff who remove clip 10 and engage screwdriver 22 with the next screw.

The second way of removing clip 10 from screw 12 is illustrated in FIG. 11 and requires that the surgeon use both of his hands. This type of clip removal would be desirable in cases where the patient has very fragile and fragmented bone. When screw 12 is sufficiently seated in bone 60, the surgeon maintains the engagement of the tip 20 of screwdriver 22 with head 14 of screw 12 and, using his other hand, grasps first section 28 of clip 10 between two fingers and pulls clip 10 upwardly along shaft 22a in the direction indicated by arrow "U". The force exerted causes head 14 of screw 12 to push clamping members 46a, 46b away from each other and allows head 14 to slide out of the opening in second end 24b of clip 10. The surgeon pulls clip 10 upwardly on shaft 22a until he has full visibility of the driver tip 20 engaged in head 14. When screw 12 is fully seated in the bone 60 and plate 62 is secured against the same, screwdriver 22 is disengaged from head and passed back to the surgical staff member.

Figure 12:
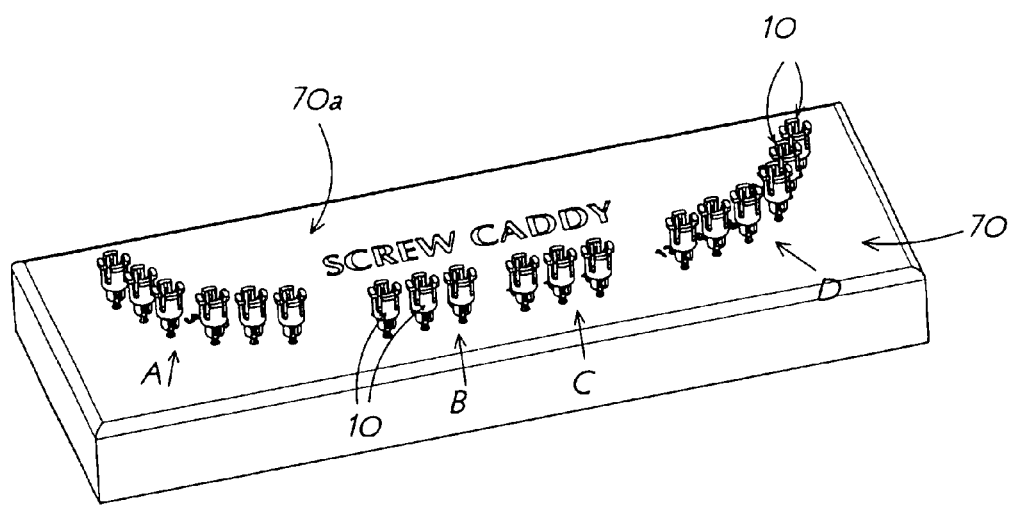
FIG. 12 is a perspective view of a screw caddy showing a plurality of retention clips engaged with a plurality of surgical screws.
Figure 13:
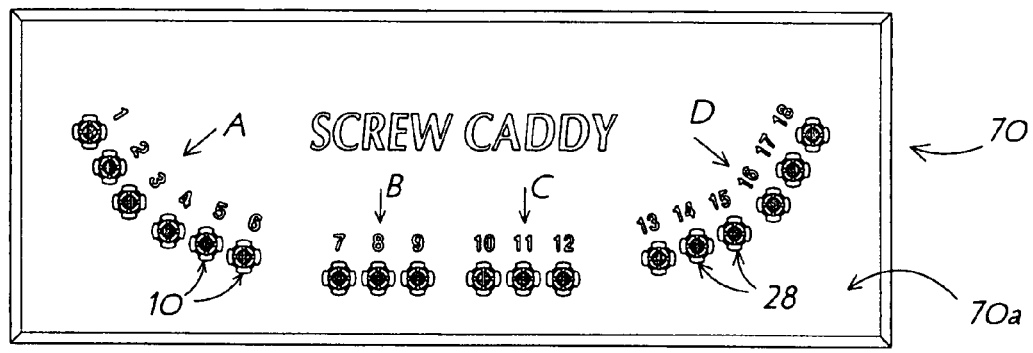
FIG. 13 is a top view of the screw caddy of FIG. 12.

It is important that the highly accurately machined titanium screw head 14 fit between clamping members 46 in clip 10 correctly. As this is a plastic part, clip 10 is designed to flex open only once to release screw head 14 therefrom. Screw 12 is therefore loaded through first end 24a of clip 10 so as not to overly stress clamping members 46 during assembly. Screw head 14 must also be able to "pop" out of clip 10 with a gentle one-handed twist of the screwdriver 22, as previously described, and must not be able to fall off inadvertently. There are therefore several ways of supplying clips 10 to the surgical team. Firstly, the titanium screw manufacturer could assemble clip 10 with screw 12 at the factory and then sterilize, package and ship the two components as an assembly. In this procedure, screw 12 would be inserted into clip 10 with head 14 of screw being snapped into channel 52 with a press. Once the assemblies are received, they can be installed into a screw caddy 70 (FIG. 12) for incorporation into a surgical kit. Alternatively, clips 10 could be shipped directly to the hospital. There, the staff would insert each screw 12 into a clip 10 and push screw 12 into the locked position between clamping members 46 with a plastic loading tool that would limit insertion travel. Then the screw and clip assemblies would be installed in caddy 70. The hospital approach is less desirable as staff could make errors with various screw heads and clip jaw sizes and overstress the clips or have clips only loosely retaining the screws therein. Thirdly, the manufacturer could install a plurality of differently sized clip and screw assemblies into screw caddy 70 and then sterilize, package and ship to the hospital where it can be incorporated into a surgical kit. Finally, the clips could be manufactured from a metal or plastic that enables them to be reused. In this instance, the clips would be sterilized, reloaded with screws and placed into screw caddy 70.

Figure 14:
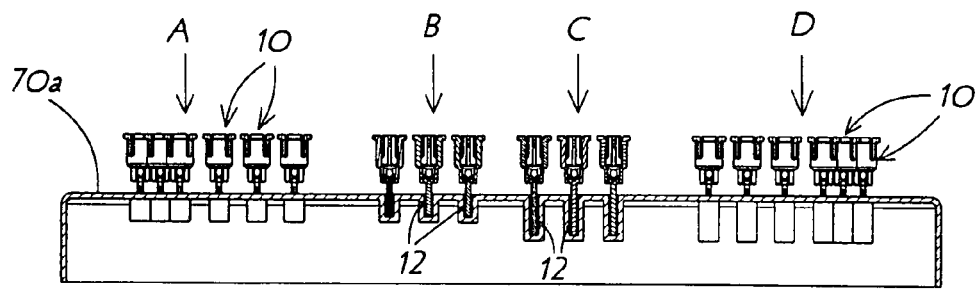
FIG. 14 is a cross-sectional front view of the screw caddy of FIG. 12.
Figure 15:
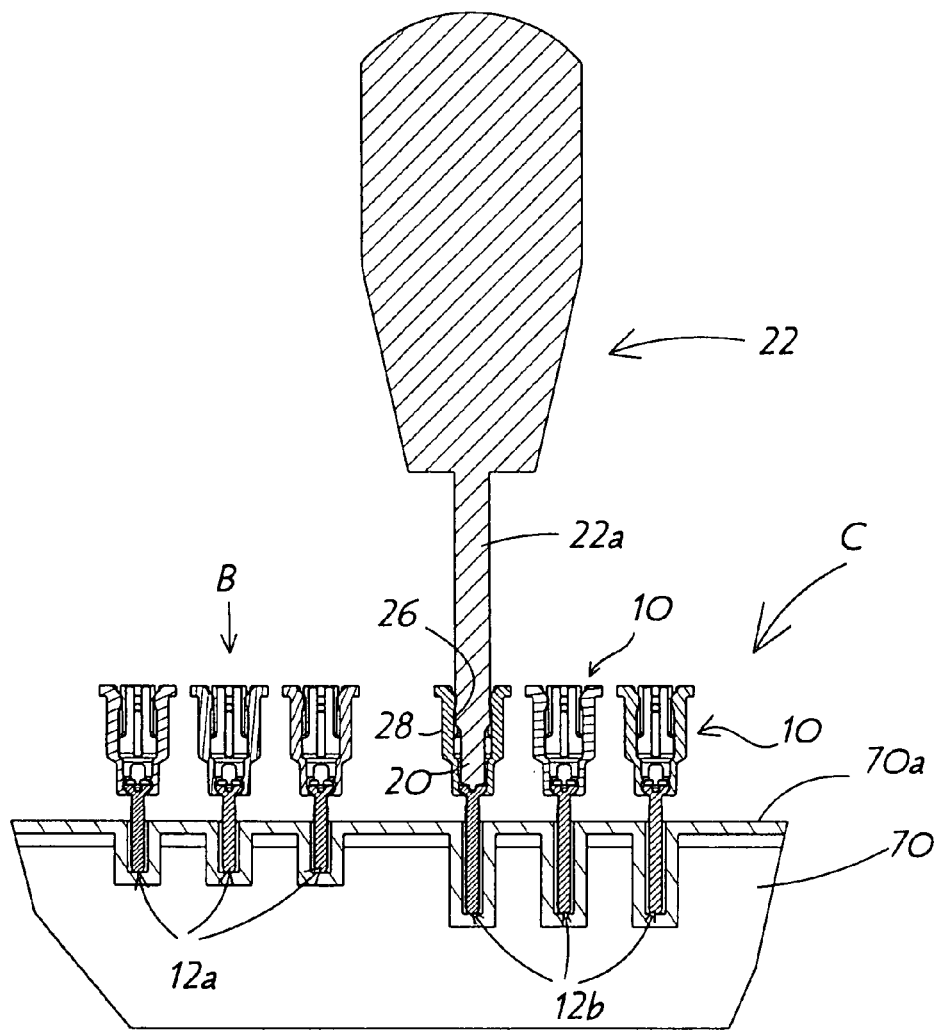
FIG. 15 is a partial cross-sectional front view of a screwdriver being engaged with one of the screws retained within the screw try.
Figure 16:
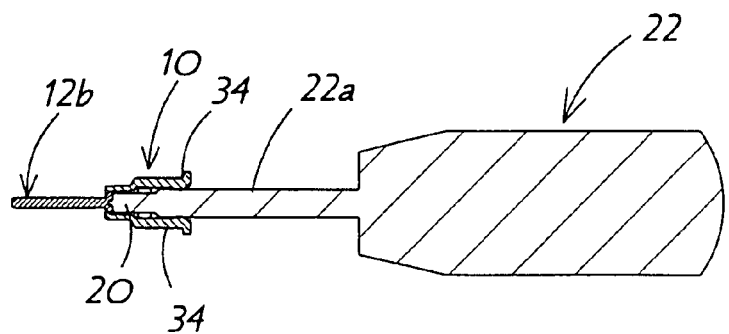
FIG. 16 is a cross-sectional front view of the screw engaged with the driver via the retention clip and showing the screwdriver in a horizontal position that ordinarily would have resulted in the dropping of the screw had the clip not been used.

FIGS. 12-16 illustrates how the surgical team would use screw caddy 70. The number of screws illustrated in caddy 70 has been reduced for the sake of clarity. Screw caddy 70 includes a plurality of different size screws such as 12a, 12b (FIG. 15). Screws 12a, 12b may be different from each other in both diameter and length. Screws 12a, 12b are grouped according to their size and length and each group is separated from the others by a gap on try 70 to make it easier for the surgical staff to locate the proper size screw needed.

In accordance with a specific feature of the present invention, each screw 12 pre-loaded in tray 70 will be engaged with one of a plurality of clips 10. Clips 10 are color-coded so that the surgical staff may more easily locate the necessary size and length screw needed for a particular procedure, even if that size screw has been accidentally positioned with a screw of the wrong length. For example, when the surgical staff receives tray 70, the first group of screws "A" (FIG. 12) may have blue clips, the second group "B" may have red clips, the third group "C" may have green clips and the fourth group "D" may have yellow clips. The surgical staff will therefore be easily able to recognize that the wrong size screw is being selected for a particular procedure. Each clip 10 is in the locked position on the heads of screws 12 secured in tray 70 and is therefore immediately ready for use by the surgical staff. Screws 12 and their associated clips 10 are all at the same height just slightly above the caddy's top surface 70a as is shown in FIG. 14. This is necessary, even though the lengths of the screws retained therein differ, as the caddy 70 must be able to slide into a specialized kit.

Once the appropriate size screw 12 is located, such as one of screws 12b (FIG. 15), then the tip 20 of screwdriver 22 is inserted into bore 26 of clip 10. The interference fit between clip 10 and shaft 22a allows the screw 12 to be removed from caddy 70 by simply pulling screwdriver 22 upwardly. Once screw 12 is removed, the surgical staff member would then hold first section 28 of clip 10 and twist screwdriver 22 to correctly engage tip 20 in groove 18 on head 14 of screw 12. Screwdriver 22 is then passed to the surgeon in any orientation without screw 12b and clip 10 becoming detached therefrom. The surgeon may also hold the screwdriver in any required orientation, such as in FIG. 16, to install screw 12b. Screw 12 is turned so that approximately 80%-90% of its length is retained in bone 60. With the screw 12 now reasonably secured to bone 60, the surgeon detaches clip 10 from screw 12 as previously described. Once the screw 12b is installed, clip 10 is removed from screwdriver shaft 22a and is kept for the final screw count. The surgical staff then inserts the screwdriver 22 into the next required screw and the procedure is repeated until the surgery is finished.

Although clip 10 is preferred to be a single-use device as the plastic flex therein can only be relied upon one time to have the exact fit and function necessary for proper operation, it is conceivable that clip 10 could be manufactured from stamped metal and would be reusable. In this latter instance, color coding could be applied to the metal in some manner.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A clip for retaining a screw on a tip of a screwdriver shaft; said clip comprising:
   a housing having a first end and a second end, and having a longitudinal axis extending therebetween;
   a bore extending longitudinally through the housing and being accessible from both the first and second ends;
   first and second pairs of jaw members provided on the housing proximate the first end thereof and surrounding a first portion of the bore; said jaw members being adapted to capture a length of the screwdriver shaft therebetween; wherein each jaw member has a first longitudinal edge and a second longitudinal edge and an inner surface extending both laterally and longitudinally therebetween;
   a rib provided on the inner surface of at least one of the jaw members, said rib having a first longitudinal side and a second longitudinal side, and the first longitudinal side of the rib is disposed a distance laterally inwardly away from the first longitudinal edge of the associated jaw member and the second longitudinal side is disposed a distance laterally inwardly away from the second longitudinal edge thereof, and wherein said rib extends for a distance radially inwardly into the bore; and
   a pair of clamping members are provided on the housing proximate the second end thereof and surrounding a second portion of the bore, said clamping members being adapted to capture a head of the screw therebetween.

2. The clip as defined in claim 1, wherein the jaw members are separated from each other by four longitudinally aligned opposed slots; said slots arising proximate the first end of the housing and extending toward the second end of the housing, wherein the jaw members each have an upper end proximate the first end of the housing; and wherein said upper ends of the jaw members are movable relative to each other; and wherein the rib extends from proximate the upper end of the at least one of the jaw members to proximate a lower end thereof.

3. The clip as defined in claim 2, wherein each jaw has an outer surface disposed opposite the inner surface thereof; and wherein the clip further comprises a flange that extends radially outwardly away from the upper end of each jaw member and beyond the outer surface thereof; and each flange is disposed substantially at right angles to the longitudinal axis of the housing.

4. The clip as defined in claim 2, wherein the slots each terminate at a terminal end, and wherein the rib extends for a distance longitudinally beyond the terminal ends of the slots.

5. The clip as defined in claim 1, further comprising:
   an innermost face provided on the rib extending between the first and second longitudinal sides thereof; wherein said innermost face is disposed a first distance radially away from the inner surface of the jaw member; and
   a protrusion provided on the innermost face of the rib and extending radially outwardly away therefrom and into the bore, wherein the protrusion has a first longitudinal side, a second longitudinal side, an upper face, a lower face, and an inner face extending therebetween, wherein said protrusion's inner face is disposed a second distance radially away from the inner surface of the jaw member and said second distance is greater than the first distance; and wherein the upper and lower faces extend respectively longitudinally upwardly and downwardly from the inner face and between the protrusion's first and second longitudinal sides, and wherein said inner face of said protrusion is adapted to engage the shaft of the screwdriver.

6. The clip as defined in claim 5, wherein a rib is provided on each jaw member; and a protrusion is provided on each one of the ribs, each protrusion being situated in a region proximate the first end of the housing such that a portion of the innermost face of each rib extends longitudinally downwardly for a length beyond the lower face of the associated protrusion and toward the second end of the housing.

7. The clip as defined in claim 1, wherein the clamping members are separated from each other by a pair of longitudinally opposed slots, said slots arising proximate the second end of the housing and extending inwardly toward the first end thereof; wherein said clamping members each terminate in a lower end; and wherein said lower ends are flexible relative to each other when the head of the screw is released therefrom.

8. The clip as defined in claim 7, further comprising an inner surface on each of the clamping members; a pair of spaced apart flanges formed on each inner surface and extending into the bore substantially at right angles to the longitudinal axis of the housing; and wherein the head of the screw is captured between said pairs of spaced apart flanges.

9. The clip as defined in claim 8, wherein the first portion of the bore is of a first diameter; and the second portion of the bore is of a second diameter, and the second diameter is smaller than the first diameter.

10. The clip as defined in claim 1, wherein the clip is manufactured from a flexible material.

11. The clip as defined in claim 10, wherein the flexible material is a plastic and the clip is injection molded therefrom.

12. The clip as defined in claim 1, wherein the clip is manufactured from a colored material having a color, said color being provided as an identifier to indicate a size of screw that the clip is adapted to retain therein.

13. The clip as defined in claim 1, wherein the ribs terminate a distance away from the clamping members.

14. The clip as defined in claim 1, wherein the bore has a wider region and a narrower region and the clip further includes an annular shoulder disposed in an area where the bore narrows from the wider region to the narrower region, and wherein the ribs originate proximate the first end of the housing and terminate proximate the shoulder.

15. The clip as defined in claim 14, wherein the jaw members originate at the first end of the housing and terminate proximate the shoulder and the clamping members originate proximate the second end of the housing and terminate proximate the shoulder.

16. The clip as defined in claim 1, further comprising:
four longitudinally aligned first slots separating the jaw members from each other, each first slot extending from the first end of the housing downwardly toward the second end thereof and terminating at a first terminal end spaced a distance from the second end of the housing; and
a pair of longitudinally aligned second slots separating the clamping members from each other, each second slot extending from the second end of the housing upwardly toward the first end thereof and terminating at a second terminal end; and wherein the second terminal ends are spaced a distance from the first terminal ends and the housing further includes an annular region disposed between the first and second terminal ends and the annular region is free of both of the first and second slots.

17. The clip as defined in claim 16, wherein the first slots are out of longitudinal alignment with the second slots.

\* \* \* \* \*